(12) United States Patent
Koren et al.

(10) Patent No.: US 12,171,796 B2
(45) Date of Patent: Dec. 24, 2024

(54) HYDROGEL WOUND TREATMENT

(71) Applicant: IZUN PHARMACEUTICALS CORP., New York, NY (US)

(72) Inventors: Nechama Koren, Jerusalem (IL); Amy Rosenbluh, Modiin (IL); William Z. Levine, Jerusalem (IL)

(73) Assignee: IZUN PHARMACEUTICALS CORP., New York, NY (US)

( * ) Notice: Subject to any disclaimer, the term of this patent is extended or adjusted under 35 U.S.C. 154(b) by 643 days.

(21) Appl. No.: 17/290,760

(22) PCT Filed: Nov. 4, 2019

(86) PCT No.: PCT/IL2019/051203
§ 371 (c)(1),
(2) Date: May 2, 2021

(87) PCT Pub. No.: WO2020/089920
PCT Pub. Date: May 7, 2020

(65) Prior Publication Data
US 2022/0175861 A1   Jun. 9, 2022

(30) Foreign Application Priority Data

Nov. 4, 2018 (IL) ........................... 262744

(51) Int. Cl.
| | | |
|---|---|---|
| *A61K 36/28* | (2006.01) | |
| *A61F 13/00* | (2024.01) | |
| *A61K 9/00* | (2006.01) | |
| *A61K 9/06* | (2006.01) | |
| *A61K 36/185* | (2006.01) | |
| *A61K 36/23* | (2006.01) | |
| *A61L 15/44* | (2006.01) | |
| *A61P 17/02* | (2006.01) | |

(52) U.S. Cl.
CPC ........ *A61K 36/28* (2013.01); *A61F 13/00063* (2013.01); *A61F 13/00072* (2013.01); *A61K 9/0014* (2013.01); *A61K 9/06* (2013.01); *A61K 36/185* (2013.01); *A61K 36/23* (2013.01); *A61L 15/44* (2013.01); *A61P 17/02* (2018.01); *A61K 2236/333* (2013.01); *A61L 2300/30* (2013.01)

(58) Field of Classification Search
CPC ........ A61K 36/28; A61K 9/0014; A61K 9/06; A61K 36/185; A61K 36/23; A61K 2236/333; A61F 13/00063; A61F 13/00072; A61L 15/44; A61L 2300/30; A61L 15/60; A61P 17/02
See application file for complete search history.

(56) References Cited

U.S. PATENT DOCUMENTS

2015/0064291 A1 * 3/2015 Rosenbluh ............. A61K 36/23
424/764

FOREIGN PATENT DOCUMENTS

| WO | 2008142619 | 11/2008 |
|---|---|---|
| WO | 2012065651 | 5/2015 |

OTHER PUBLICATIONS

Oberbaum et al "Inhibition of Matrix Metalloproteinase Activity by a Transmucosal Patch Containing Botanical Compounds" Dent Oral Craniofac Res 2:2(5): 349-354.
Reddy et al "Efficacy of Periopatchtm—Intra-Oral Wound Dressing as Adjunct to SRP in Treatment of Periodontitis"4, 4(4), 1-7.

* cited by examiner

*Primary Examiner* — Robert A Wax
*Assistant Examiner* — Quanglong N Truong
(74) *Attorney, Agent, or Firm* — JMB Davis Ben-David (57) ABSTRACT

Described herein are hydrogel compositions comprising extracts of *Sambucus nigra*, *Centella asiatica* and *Echinacea purpurea*. The compositions were found to have improved wound-healing effects. Also described herein are methods for treatment of a wound comprising administering, topically to a patient in need thereof, a therapeutically effective amount of a hydrogel composition comprising extracts of *Sambucus nigra*, *Centella asiatica* and *Echinacea purpurea*.

20 Claims, 2 Drawing Sheets

HYDROGEL WOUND TREATMENT

CROSS REFERENCE TO RELATED APPLICATIONS

This is the U.S. National Stage of International Patent Application No. PCT/IL2019/051203, filed on Nov. 4, 2019, which in turn claims the benefit of Israel Application 262744 filed Nov. 4, 2018; the contents of which is incorporated by reference herein in its entirety.

FIELD

Provided herein are compositions for treating wounds and traumatic injuries and methods for treatment using the compositions.

BACKGROUND

Wound healing is the process in which the skin heals itself after injury. Wounds in mammalian patients may be caused by various causes including impact by a sharp object, cutting the skin, or burns. Additionally, wounds may include ulcers such as pressure ulcers or diabetic ulcers such as diabetic foot or leg ulcers. Ulcers are sores on the skin in which the surface tissue is lost and the underlying tissue is affected and often inflamed.

Pressure ulcers, also known as pressure sores or bedsores, are wounds caused by prolonged pressure applied to soft tissue in localized areas of the body, primarily in skin covering bony regions of the body. Pressure ulcers are commonly found in bedridden patients and in areas of skin to which constant pressure is applied. Moisture in the region of the ulcer stemming from patient's bodily fluids may cause and/or exacerbate a pressure ulcer.

Diabetic foot ulcers are complications of diabetes. In patients suffering from diabetes, some stages of wound healing are slowed. Diabetic foot and leg ulcers, if untreated, may become infected and lead to amputation.

Additional types of wounds include traumatic wounds and surgical wounds. Some of these wounds do not heal properly and become chronic for many reasons.

Excessive inflammation also prevents wound healing and is the source of non-healing wounds in the oral cavity, in the anal region, and in other areas of the body.

In addition to physical discomfort and aesthetic disadvantages in patients suffering from wounds, all non-healing wounds are at high risk of infection, which can lead to potentially life-threatening complications.

SUMMARY

Described herein are hydrogel compositions comprising extracts of *Sambucus nigra, Centella asiatica* and *Echinacea purpurea*. The compositions were found to have a synergistic effect to generate improved wound-healing effects.

Also described herein are methods for treatment of a wound comprising administering, topically to a patient in need thereof, a therapeutically effective amount of a hydrogel composition comprising extracts of *Sambucus nigra, Centella asiatica* and *Echinacea purpurea*.

The foregoing and other objects, features, and advantages will become more apparent from the following detailed description, which proceeds with reference to the accompanying figures.

DETAILED DESCRIPTION

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Definitions of common terms in pharmaceutical sciences can be found in Troy et al. *Remington: The Science and Practice of Pharmacy*. Published by Lippincott Williams & Wilkins, 2006. In case of conflict, the present specification, including explanations of terms, will control. In addition, all the materials, methods, and examples are illustrative and not intended to be limiting.

Definitions

Alcoholic extract: An extract of a botanical product produced using at least 50% alcohol. An exemplary alcohol may be ethanol.

Anal fissure: A small tear in the mucosal lining the anus. Anal fissures may be acute or chronic. Anal fissures may be considered chronic after not healing for two months.

Arterial ulcer: Wounds that form typically on the outer side of the ankle, feet, heels or toes, typically caused by clogged or blocked arteries in the leg, preventing nutrient-rich blood from reaching the area of the ulcer.

Diabetic ulcer: in diabetes mellitus, in particular in older patients, diabetic ulcers on the feet are often formed. It has been suggested that metabolic changes in diabetes patients negatively impact granulation tissue formation, and pro-inflammatory cytokines present in diabetic ulcers negatively impact wound repair.

Granulation: Granulation is evident when new connective tissue and tiny blood vessels form on the surfaces of a wound during the healing process.

Joint Inflammation: Swelling of the joints which may be caused by trauma, infection or autoimmune disease.

Leg ulcer of mixed etiology: Leg wounds which stem from both a venous and arterial component.

Oral wounds: Wounds of the oral cavity. In particular, oral wounds such as chronic periodontal disease or wounds that may follow periodontal surgery, dental implantation or dental extraction. Osteonecrosis of the jaw: A bone disease occurring in the maxilla and/or mandible in which a subject has lesions exposing bone.

Pressure ulcers: injuries to skin and/or surrounding tissue caused by prolonged pressure to the skin.

Stoma: an opening in the body caused by a surgical procedure such as colostomy.

Traumatic wounds: cuts or puncture wounds that penetrate the skin. May be caused by incision, abrasion, animal bites, and other causes in which the skin is forcefully impacted.

Venous stasis ulcer: Wounds typically occurring along the medial or lateral lower leg. They result from malfunctioning venous valves causing internal vein pressure to increase, thereby allowing fluid to exude into subcutaneous tissue.

Provided herein are hydrogel compositions that provide an environment that is supportive to wound healing. Upon topical application to a wound, the hydrogel composition may assist in removal in excess fluids stemming from a patient's bodily fluids, while maintaining a moist environment in and around the wound. This makes the hydrogel effective in protecting the wound and assisting the debridement and desloughing process in dry necrotic wounds, while maintaining a moist wound environment for optimal wound healing.

Optionally, the hydrogel may be used in internal wounds such as joint inflammation or a stoma created through an ostomy.

According to an embodiment, the compositions comprise a sterile, amorphous hydrogel containing a high water content and hydrophilic polymer chains. Without being bound by theory, it is suggested that the compositions assist in management of partial and full thickness wounds by providing a moist environment for healing of the wound. The high water content may help regulate fluid exchange from the wound surface. It is suggested that hydrogel compositions according to some embodiments create a moist healing environment by providing moisture that promotes the healing process at the wound site. The hydrogel also absorbs inflammatory exudates to reduce matrix metalloproteinases (MMP's) and other pro-inflammatory mediators. This moist healing environment and reduction of inflammatory mediators promotes granulation, epithelialization, collagen formation and autolytic debridement. Due to the high water-content of hydrogel dressings, the hydrogel also cools the wound and provides pain relief. These gels may also have an acidic environment, which can help prevent the growth of microorganisms that can lead to infection.

According to an embodiment, the composition comprises between about 1% and about 30% of extract blend of *Sambucus nigra, Centella asiatica* and *Echinacea purpurea*. According to an embodiment, the composition comprises about 7% of blend extract of *Sambucus nigra, Centella asiatica* and *Echinacea purpurea*. According to an embodiment, the extract blend of *Sambucus nigra, Centella asiatica* and *Echinacea purpurea* is an aqueous extract. According to an embodiment, the blend extract of *Sambucus nigra, Centella asiatica* and *Echinacea purpurea* is a secondary extract formed from alcoholic extract of the aforementioned botanical ingredients.

According to an embodiment, the extracts *Sambucus nigra, Centella asiatica* and *Echinacea purpurea* are present in the composition in a ratio of about 7:2:1 *Sambucus nigra, Centella asiatica* and *Echinacea purpurea*.

According to an embodiment, the water content of the hydrogel composition is above 50%. According to an embodiment, the water content is between 60% and 85%.

According to an embodiment, the composition comprises a gelling agent selected from the group consisting of propylene glycol, guar gum, alginic acid, sodium alginate, potassium alginate, ammonium alginate, calcium alginate, agar, carrageenan, and gelatin.

According to an embodiment, the composition comprises a carrier. The carrier may be maltodextrin.

Provided herein are methods for treatment using compositions described herein. Methods of treatment may include administering to a patient in need thereof, a composition, for treatment of a wound. The wound may be selected from the group consisting of: diabetic foot ulcers, leg ulcers, pressure ulcers/sores, and 1st and 2nd degree partial thickness burns, a surgical wound, traumatic wounds, periodontal disease, anal fissure and hemorrhoids, stoma apertures due to ostomy, and joint inflammation. The leg ulcer may be a venous stasis ulcer, an arterial ulcer or a leg ulcer of mixed etiology. The pressure ulcer may be an ulcer of partial or full thickness.

The wound may be selected from the group consisting of a wound as a result of acute trauma, a minor abrasion, a minor laceration, a minor cut, a minor scald and a minor burn.

It is suggested that hydrogel compositions comprising extracts of *Sambucus nigra, Centella asiatica*, and *Echinacea purpurea* be applied multiple times to an area of a wound. Optionally, the composition is applied between 2 and 3 times per week for chronic wounds but can be applied more frequently if needed.

Before application, the wound and surrounding skin is cleaned and blotted dry. A thin layer of composition sufficient to cover the wound base and any necrotic tissue is applied, minimizing overlap onto the surrounding skin. Optionally, the thin layer is applied in a thickness of about 2 mm.

The wound may then be covered with a moistened gauze bandage. The composition may be left in place for up to 4 days. The dressing may be changed as needed, depending on factors such as the type of wound and volume of drainage. Remaining hydrogel at the time of removal of dressing may be rinsed away with wound cleanser or sterile normal saline as necessary. The composition may be applied again as described until complete wound closure is achieved.

The following examples are provided to illustrate certain particular features and/or embodiments. These examples should not be construed to limit the disclosure to the particular features or embodiments described.

Example 1

Synthesis of Hydrogel

A hydrogel was formed using the components listed in Table 1:

TABLE 1

| Component | Amount (% w/w) | Function |
|---|---|---|
| Sambucus nigra extract | 4.90 | Antimicrobial and pH control |
| Centella asiatica extract | 1.40 | Antimicrobial and pH control |
| Echinacea purpurea extract | 0.70 | Antimicrobial and pH control |
| Maltodextrin | 3.00 | Carrier |
| RO water | 74.00 | Solvent/Hydrating agent |
| Guar Gum | 2.48 | Gelling agent |
| Propylene glycol | 13.49 | Gelling agent |
| Borax | 0.01 | Crosslinking agent |

Ethanolic extracts were prepared and dried separately from each of (i) *Sambucus nigra* flos, (ii) *Centella asiatica* herba and (iii) *Echinacea purpurea* radix, as follows:

*Sambucus nigra* (flowering tops) was extracted through a hydro-alcoholic process. Upon removing insoluble plant matter and drying solvent, dried *Sambucus nigra* extract was formed. The same was done for *Centella asiatica* (aerial parts) and *Echinacea purpurea* (rhizome and roots).

The three dried extracts were well blended (i:ii:iii) in a ratio of 7:2:1. The blend of ethanolic extracts was water-extracted. The water-insoluble materials were removed, and the water-soluble materials were dried to form an active biological ingredient (ABI). The ABI was dissolved in water.

Guar gum, propylene glycol, and borax were mixed and the mixture was added to the water+ABI solution and mixed until gelled.

Gel was then dispensed into tubes. Tubes were sealed and sterilized using steam sterilization.

Example 2A: Stability Testing of Hydrogel

Hydrogels prepared as in example 1 were stored at 40° C. at 75% relative humidity (RH) for 6 months and at 25° C. at 60% RH for 42 months and the following results were found:

The amber color and herbal aroma were maintained. The pH remained below 6.0, and was stable at 5.0. The concentrations of the chemical markers contained in *Sambucus nigra*, *Centella asiatica*, and *Echinacea purpurea*, respectively, remained greater than 75% of the starting concentration. Viscosity remained greater than or equal to 100,000 centipoise (cPs). Not more than 100 Colony Forming Units (CFU)/g total viable aerobic counts were observed. Not more than 10 CFU/g total yeasts and molds were observed. There was an absence of *P. aeruginosa* and *S. aureus*.

Additionally, compositions prepared as in example 1 may be prepared as sterile products, for example, by heating. In such sealed compositions, there is no observed microbial growth.

Example 2B: Physical Characteristics of Hydrogel: Rheology

Viscosity characteristics and soft-solid structure of hydrogel prepared according to example 1 and FlexiGel-G Hydrogel Dressing. FlexiGel-G™ (ActivHeal) Hydrogel Wound Dressing is a commercially available hydrogel (Advanced Medical Solutions, Winsford, Cheshire, United Kingdom) comprising guar gum, borax, propylene glycol and water. It has a pH of 6.2 and is approved for wound care in the US.

The viscosity of two batches of hydrogel of example 1 was tested and found to be between 110,000 and 120,000 centipoise (cps), whereas the viscosity of FlexiGel-G Hydrogel Dressing was determined to be over 120,000.

Further analysis was performed at the Center for Industrial Rheology (Warnford, Hampshire UK). The samples were exposed to the following conditions:
1. Oscillation stress sweeps that ranged from 0.1 Pa to 1000 Pa, 1 Hz oscillation frequency at 25° C.
2. Controlled rate viscosity profiles by a shear rate down-sweep at 300 $s^{-1}$ to 10 $s^{-1}$ that was logarithmically scaled, 8 points per decade of shear rate at 31° C.

The data of both samples demonstrated structured liquid-like behavior with a soft solid structure yielding oscillation stress sweeps to a non-Newtonian, shear thinning viscous flow (controlled rate viscosity profiles). Data from Flexi-Gel-G Hydrogel Dressing experiments showed that it had higher viscosity across all shear rates and that oscillation stress sweeps revealed it had a more rigid gel and a lower phase angle plateau indicating a more developed elastic structure.

The rheology analysis showed that the hydrogel according to example 1 has a lower yield stress and lower viscosity when compared to FlexiGel-G Hydrogel Dressing. Such properties contribute to the more spreadable attributes of hydrogels described herein and the greater ease with which it is applied to the skin when compared to FlexiGel-G Hydrogel Dressing. Furthermore, without being bound by theory, it is suggested that the lower viscosity allows for the dressing to be applied with greater ease without disturbing the natural healing process of the wound. In addition, the wound surface is irregular and so the lower viscosity allows for an improved adaptation of the gel to the wound surface which is expected to improve the physiologic response.

Example 2C: Physical Characteristics of Hydrogel: pH

Two batches of hydrogel composition prepared according to Example 1, and two batches of FlexiGel-G Hydrogel Dressing were tested for pH using a calibrated electrode.

The results of the pH testing of the two batches of hydrogel composition prepared according to Example 1 were pH of 5.19 and 5.17, respectively. The results of the pH testing of the two batches of FlexiGel-G Hydrogel Dressing were 6.05 and 6.09, respectively.

These results indicate that the ABI has a potential pH lowering effect to the hydrogel, which contributes to its wound healing relative to the hydrogel without the ABI present.

Example 3A: Testing of In Vitro Characteristics of Hydrogel (Antimicrobial and Inflammatory Assay)

Antimicrobial Assay:

An antimicrobial assay was performed using a hydrogel composition prepared according to Example 1. As a control, a test composition hydrogel, commercially available Flexi-Gel-G™ (ActivHeal) Hydrogel Wound Dressing was used.

FlexiGel-G™ (ActivHeal) Hydrogel Wound Dressing is a commercially available hydrogel (Advanced Medical Solutions, Winsford, Cheshire, United Kingdom) comprising guar gum, borax, propylene glycol and water. It has a pH of 6.2 and is approved for wound care in the US.

The antimicrobial assay was performed in accordance with the United States Pharmacopeia, section 51. The assay involved inoculating test items with quantities of microorganisms as listed in Table 2, and then testing for presence and quantity of microorganisms at various time periods. Table 2 shows results of antimicrobial effectiveness at time points between 1-4 weeks of FlexiGel-G™ (ActivHeal) Hydrogel after inoculation with various microorganisms.

TABLE 2

| Test Organism | ATCC # | Initial inoculation CFU/g | No. of Surviving Microorganisms CFU/g | | | |
|---|---|---|---|---|---|---|
| | | | 1 week | 2 week | 3 week | 4 week |
| Escherichia coli | 8739 | $3.9 \times 10^5$ | $2.6 \times 10^2$ | <10 | <10 | <10 |
| Staphylococcus aureus | 6538 | $3.3 \times 10^6$ | $6.7 \times 10^5$ | $2.8 \times 10^4$ | $5.9 \times 10^3$ | $1.2 \times 10^2$ |
| Pseudomonas aeruginosa | 9027 | $4.4 \times 10^6$ | $1.8 \times 10^2$ | <10 | <10 | <10 |
| Candida albicans | 10231 | $3.7 \times 10^6$ | $3.1 \times 10^6$ | $4.5 \times 10^6$ | $3.8 \times 10^6$ | $3.5 \times 10^6$ |
| Aspergillus brasiliensis | 16404 | $1.8 \times 10^6$ | $1.0 \times 10^6$ | $8.0 \times 10^5$ | $7.0 \times 10^5$ | $8.0 \times 10^5$ |
| Uninoculated control | N/A | N/A | <10 | <10 | <10 | <10 |

Table 3 shows results of antimicrobial effectiveness at time points between 1-4 weeks of the hydrogel composition prepared according to Example 1, after inoculation with various microorganisms

TABLE 3

| Test Organism | ATCC | Initial Contamination CFU/g | No. of Surviving Microorganisms CFU/g | | | |
|---|---|---|---|---|---|---|
| | | | 1 week | 2 week | 3 week | 4 week |
| Escherichia coli | 8739 | $3.9 \times 10^5$ | <10 | <10 | <10 | <10 |
| Staphylococcus aureus | 6538 | $3.3 \times 10^6$ | <10 | <10 | <10 | <10 |
| Pseudomonas aeruginosa | 9027 | $4.4 \times 10^6$ | <10 | <10 | <10 | <10 |
| Candida albicans | 10231 | $3.7 \times 10^6$ | $2.9 \times 10^6$ | $3.2 \times 10^6$ | $2.8 \times 10^6$ | $3.4 \times 10^6$ |
| Aspergillus brasiliensis | 16404 | $1.8 \times 10^6$ | $9.0 \times 10^5$ | $7.0 \times 10^5$ | $6.0 \times 10^5$ | $7.0 \times 10^5$ |
| Uninoculated control | N/A | N/A | <10 | <10 | <10 | <10 |

As can be seen from Tables 2 and 3, after one week, hydrogel composition prepared according to Example 1 is effective in entirely eliminating 3 of the 5 microorganisms tested. This effect is not found in hydrogel which does not contain extracts of *Sambucus nigra, Centella asiatica* and *Echinacea purpurea*. The anti-microbial effect continues throughout the 4-week testing period. This indicates that compositions of Example 1 are surprisingly advantageous antimicrobial agents which prevent microbial growth to a greater extent than commercially available wound dressings.

Example 3B: Inflammatory Assay

Caspase-1, also called IL-1β converting enzyme (ICE), is a member of a family of nine cysteine proteases that specifically recognize an aspartic acid residue in the P1 position of their respective substrates. ICE is a critical enzyme in the inflammatory response since it cleaves the precursors of IL-1β, IL-18, and IL-33 which are well known pro-inflammatory mediators. Indeed, the rate-limiting step in inflammation due to IL-1β or IL-18 is the activation of ICE. The assay that measures ICE activity is based on a fluorogenic substrate that is specifically cleaved by ICE (also known as caspase-1), releasing 7-amino-4-methyl coumarin (AMC), which produces a yellow-green fluorescence detectable at EX360, EM460. Direct inhibition of ICE by the botanical extracts is measured in a cell-free assay.

The test materials are incubated for 30 min at 30° C. in the presence of ICE. Subsequently, the fluorogenic substrate is added, samples are incubated an additional 60 min at 30° C. and then the plate is read using a GENios plate reader (Tecan, Switzerland) at EX360, EM460. A positive control well, without any test material, is used to measure maximum ICE activity. This value was used to calculate percent inhibition.

In this assay, a composition prepared as in Example 1 (designated "Curasite") was compared to a hydrogel without ABI (designated "hydrogel only") and to the ABI in an aqueous solution (designated "Botanical Extract".) Two concentrations of compositions of hydrogels were tested, and corresponding aqueous botanical extracts were tested, at the concentrations of 0.5 and 0.25 mg/ml.

Figure 1:
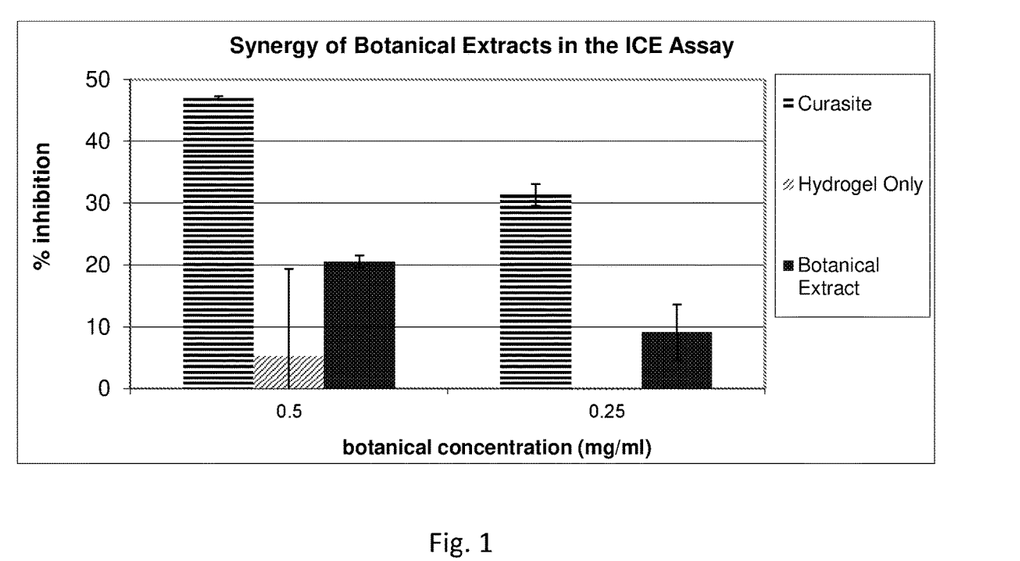
FIG. 1 depicts a bar chart showing the inhibition of IL-1β converting enzyme (ICE), using a hydrogel comprising an extract blend of *Sambucus nigra, Centella asiatica* and *Echinacea purpurea* extracts Active Botanical Ingredients (ABI) at two concentrations in an in vitro model, as compared to ABI alone without hydrogel, and hydrogel alone, without ABI.

FIG. 1 depicts a bar chart showing the ICE inhibitory data obtained for the tested compositions. The inhibitory effect of hydrogel only was low. The ABI inhibition at both concentrations was also low. However, the hydrogel combined with the ABI (Curasite) components have a synergistic, significantly increased inhibitory effect on ICE than would be obtained from the expected additive effect. This can be seen at both 0.5 mg/ml and 0.25 mg/ml concentrations.

Example 3C: Nitric Oxide (NO) Assay

Macrophages possess an inducible form of the enzyme nitric oxide synthetase (iNOS) that catalyzes the production of NO from L-arginine through two sequential oxygenation steps. Upon activation in vitro with pro-inflammatory stimuli such as LPS, iNOS expression is up-regulated and macrophages release NO to the culture medium. We stimulated macrophages with a dual inflammatory signal, LPS mixed with interferon-γ (IFN-γ).

RAW 264.7 cells were plated in 96 well plates and incubated overnight in a 5% $CO_2$, humidified incubator at 37 C. Medium was removed and replaced with serum-free DMEM and the cells were incubated for a further 1 hour. The cells were then stimulated by the addition of LPS+ recombinant IFN-γ. Inhibition was assayed by the simultaneous addition of stimulant and botanical extract/Curasite/Hydrogel. At 24 hours the conditioned medium was removed and tested for NO2- by the sequential addition of Griess reagent according to manufacturer's instructions. A reference curve was established using dilutions of a 100 micromolar solution of nitrite (Promega, Madison, WI, USA). The color produced was detected at 540 nm using a Multiskan RC plate reader (Thermo Labsystems, Finland). Color intensity is directly proportional to the amount of NO produced.

Figure 2:
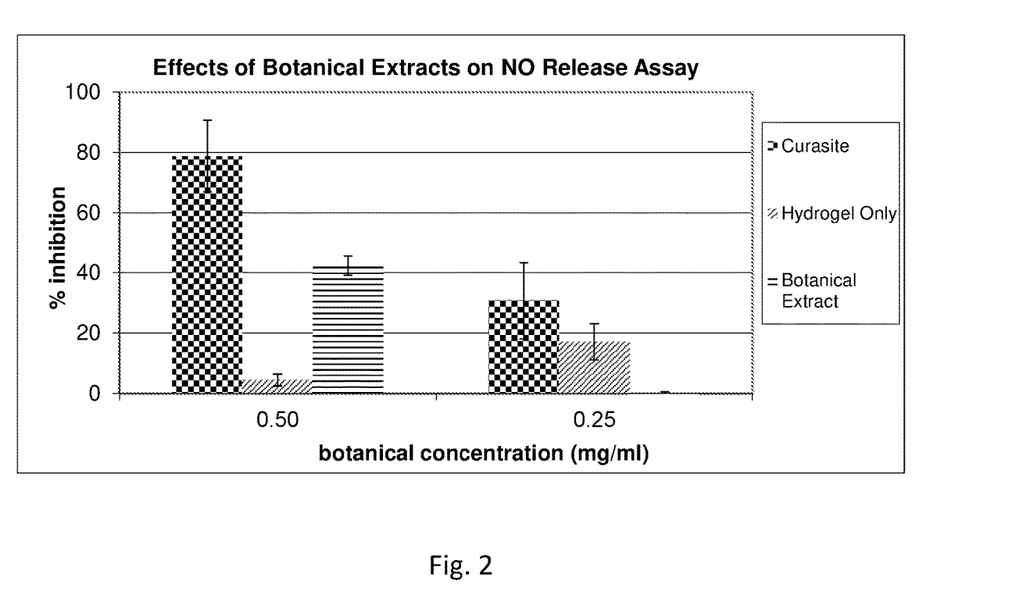
FIG. 2 depicts a bar chart showing the inhibition of Nitric Oxide (NO) release in an assay using a hydrogel comprising an extract blend of *Sambucus nigra, Centella asiatica* and *Echinacea purpurea* extracts Active Botanical Ingredients (ABI) at two concentrations in an in vitro model, as compared to ABI alone without hydrogel, and hydrogel alone, without ABI.
Figure 3:
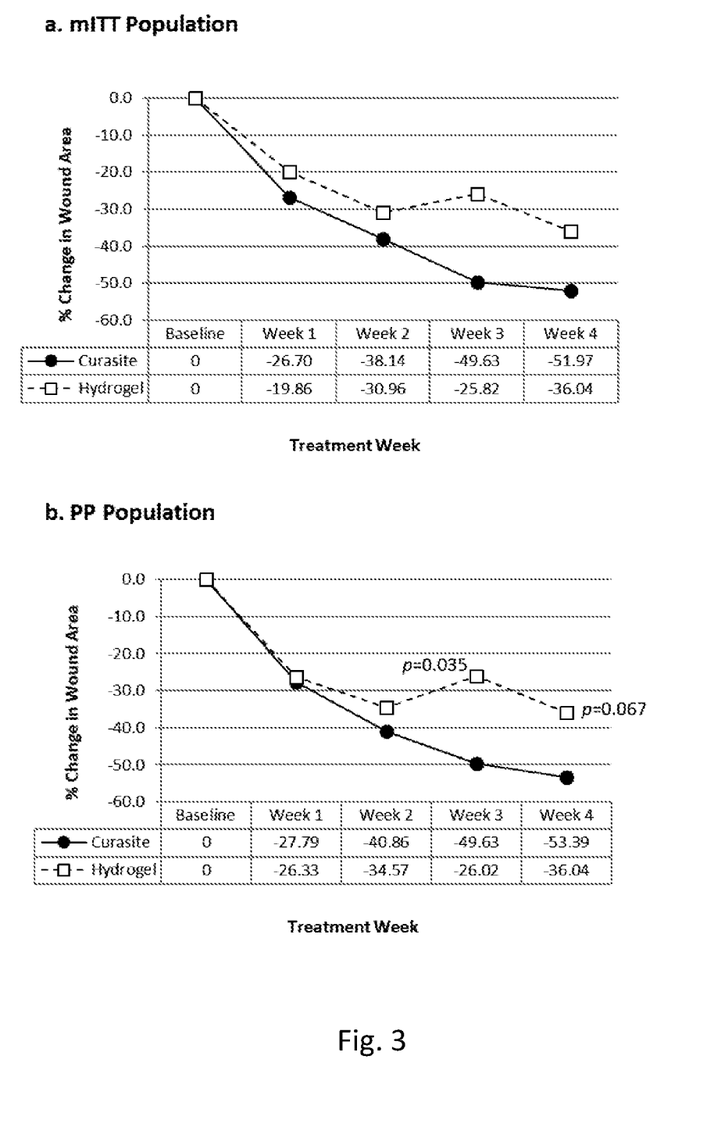
FIG. 3 depicts graphs showing decrease in wound area over a 4 week blinded treatment period in patients in two populations (a and b) suffering from wounds, after being administered either hydrogel compositions comprising *Sambucus nigra, Centella asiatica* and *Echinacea purpurea* extracts (designated as "Curasite") or hydrogel without the ABI extract blends (designated as "Hydrogel").

FIG. 2 depicts a bar chart showing the NO inhibitory data obtained for (i) Curasite, (ii) hydrogel without added botanicals, and (iii) and to the ABI in an aqueous solution (designated "Botanical Extract"). It can be seen that the components of Curasite, (ABI+hydrogel), when combined, synergize, giving Curasite a significantly increased inhibitory effect on NO than would be expected from an additive effect only. This can be seen at the two concentrations in the linear range, 0.5 mg/ml and 0.25 mg/ml.

Example 3D: Wound Healing Effect Testing in Healthy Mice

The potential of wound healing of composition prepared according to Example 1 was determined using a model in which two full-thickness skin wounds were induced on male mice. Composition 1, as prepared in Example 1, Composition 2 (Hydrogel dressing without ABI), and Saline (Control) were used to treat the wounds. The entire wounded test sites were then continuously covered with one of the test materials and were assessed at 3, 7, 11 and 15 days post-wounding. For those mice that had scheduled termination at 7, 11 and 15 days the wound was assessed prior to termination. For all other mice the wound was assessed and a new dressing of the respective test material was applied in the same manner as previously applied. The assessments included clinical signs (changes in skin, fur, eyes, mucous membranes, etc.), changes in body weight, wound area measurements, healing rate (% of wound closure), and collection and fixation of wound site biopsies and slide preparation for sponsor testing.

The results of the study showed that there was no evidence of toxicity associated with any of the test articles. Test articles demonstrated increased percent wound closure over the period of the study when compared to the control. This animal study demonstrated that Composition 1 aids in wound healing in acute wounds in healthy mice.

TABLE 4

Mean Wound Closure (%) on Study Days

| Test Material | Dose | Day 3 | Day 7 | Day 11 | Day 15 |
|---|---|---|---|---|---|
| Saline | 0.3 ml | 10.7 ± 3.83 (n = 12) | 35.6 ± 12.97 (n = 9) | 63.1 ± 4.97 (n = 6) | 81.3 ± 1.19 (n = 3) |
| Composition 2 | 0.3 g | 12.3 ± 6.07 (n = 12) | 34.4 ± 8.41 (n = 9) | 59.2 ± 5.82 (n = 6) | 83.4 ± 4.17 (n = 3) |
| Composition 1 | 0.3 g | 15.7 ± 7.34 (n = 12) | 41.4 ± 6.67 (n = 9) | 76.3* ± 5.78 (n = 6) | 90.9* ± 1.98 (n = 3) |

*$p < 0.01$ vs. Saline Control (one-way ANOVA, Dunnett multiple comparisons test)

Example 3E: Wound Healing Effect in Diabetic Mice

The potential of wound healing of composition 1 prepared according to Example 1 was determined using a model in two full-thickness skin wounds on female diabetic mice. Twelve mice were treated with composition 1, composition 2, or composition 3 to treat the wounds.

Composition 3 was prepared by using a blend of ethanolic extracts of Example 1, but without performing the secondary water extraction step, the ethanolic extracts were combined directly with the other components of the hydrogel The entire wounded test sites were then continuously covered with one of the test materials. The average percent wound closure on day 23 for the Composition 2 was 80.7%, for the Composition 1 was 83.9%, and for the Composition 3 was 70.9%. In addition, the wound size was significantly reduced from approximately 30 $mm^2$ to an average of 5.8 $mm^2$ for the Composition 2, 4.8 $mm^2$ for the Composition 1 and 8.8 $mm^2$ for the Composition 3.

TABLE 5

Mean Wound Closure (%) on Study Days

| Test Material | Dose (g/animal) | Day 4 | Day 8 | Day 12 | Day 16 | Day 20 | Day 23 |
|---|---|---|---|---|---|---|---|
| Composition 2 | 0.3 | 2.3 ± 1.33 (n = 12) | 10.4 ± 3.11 (n = 12) | 31.7 ± 8.30 (n = 8) | 50.0 ± 10.16 (n = 8) | 70.7 ± 8.61 (n = 4) | 80.7 ± 6.03 (n = 4) |
| Composition 1 | 0.3 | 9.2** ± 2.91 (n = 12) | 23.0** ± 6.32 (n = 12) | 43.2* ± 10.11 (n = 8) | 64.9* ± 9.95 (n = 8) | 75.2 ± 7.47 (n = 4) | 83.9 ± 5.30 (n = 4) |

*$P < 0.05$ vs. Reference Item (1-Way ANOVA, Dunnett Multiple Comparisons Test)
**$P < 0.01$ vs. Reference Item (1-Way ANOVA, Dunnett Multiple Comparisons Test)

The results of the study showed there was no evidence of toxicity associated with any of the test articles. Furthermore, the study demonstrates that surprisingly, composition 1 promotes significant healing in diabetic mice to a greater extent than composition 2, without ABI, and to a greater extent than composition 3, which comprises botanical ingredients which did not undergo water extraction.

Composition 1 provides rapid wound healing, especially early in the healing process (days 4-16) relative to composition 2, indicating that the composition 1 is especially effective in enhancement of granulation.

Example 4A: Use of Hydrogel in Human Subjects

An observational study was performed to determine the efficacy of a hydrogel containing botanicals as described in example 1, in treating diabetic foot ulcers (DFU). Fifteen patients with DFU were enrolled. To qualify for enrollment, patients had to have confirmed diabetes, be between the ages of 18-75 years, and have foot ulcers categorized as equal to or worse than grade 1A (non-infected, non-ischemic superficial ulceration) based on the University of Texas Health Science Center, San Antonio scale (UTHSC). Exclusion criteria included sensitivity to any of the ingredients in the hydrogel or the botanical ingredient, inability to apply the preparation to the wound site, pregnancy or the desire to become pregnant, and moderate to severe peripheral vascular disease. The duration of treatment with the hydrogel was 21 days. The study was reviewed and approved by the Institutional Review Board of the Shaare Zedek Medical Center and complied with the most recent amended Declaration of Helsinki developed by the World Medical Organization.

The hydrogel was applied by the study physician as a 2 mm thin layer covering the entire wound bed. The hydrogel was subsequently covered by a sterile saline-soaked gauze and fixed in place. Fifteen patients with DFU were enrolled. The study was conducted at the Shaare Zedek Medical Center and Jerusalem Wound Care Center.

Day 1: On the first day of the study, the patient was enrolled and baseline statistics were obtained, including the location of the ulcer, measurements of the depth and width of the lesion, and the UTHSC classification. The wound was debrided according to standard podiatric procedures, and the test substance was applied and covered with a saline dressing.

Treatment Period: Subsequently, patients returned every 3-4 days for assessment by the physician, further debridement, and application of new test substance.

End of Treatment: A comprehensive assessment was performed on day 21.

Follow-up: When possible, patients were followed for a period of up to 12 weeks.

Wound Evaluation: Several methods were used to evaluate the wound. The depth of the wound was measured with a standard calibrated probe. Surface area of the wound was assessed using a wound grid (Convatec). Digital photographs (three photographs at magnifications of 1×, 2×, 3× of increasing magnification) at a fixed distance from the wound were obtained. Qualitative assessment of tissue content and quality of healing was performed by the clinical investigator who visually estimated the percentage of wound area consisting of each of the following tissue types: necrotic, fibrotic, granulation, and epithelialized. Data were recorded on case report forms for each patient and subsequently entered in a Microsoft Excel spreadsheet. Additional data were obtained regarding adverse events that could be potentially related to the test drug. Compliance was assessed by monitoring attendance during the scheduled visits. Patients who failed to maintain their scheduled visits were released from the study.

There were several outcome variables for this observational study that were assessed at 21 days and included the number of patients with complete healing, percent change in either surface area or depth of wound during the course of the study, changes in UTSHC grade, the speed of healing in terms of reduction of wound surface area and depth over time, and subjective evaluation of wound healing based on granulation tissue. For long-term follow-up, the main outcome variable was closure. An intention to treat standard was utilized in the sense that patients lost to follow-up before complete healing were considered as treatment failures.

A complete data set for the 15 patients was obtained at 3 weeks. No serious adverse events related to the medication were recorded. Treatment with hydrogel was well tolerated among all the patients regardless of extent or severity of their ulcers. The results of treatment with hydrogel combined with conventional treatment for three weeks are summarized in Table 6 below. All subjects responded to treatment in terms of reduction of the size of their ulcers. The mean surface area of the ulcer decreased from 6.08±6.54 to 3.01±5.08 cm$^2$ (p<0.0001, t test for two-tailed paired samples). In terms of wound closure, 27% demonstrated complete closure during the three weeks, while 40% of the subjects demonstrated 75% or greater closure. Since initial wound size varied, percent wound reduction was also analyzed. The average reduction of ulcer size was 67.7%. Another indication of the efficacy of hydrogel according to example 1 was the extent of conversion of the wound tissue to granulation tissue. Granulation is an important stage in the healing process, and 14/15 patients had complete granulation of their wounds. The impact of granulation is also demonstrated by the fact that all 4 patients with deep ulcers classified as Stage 2 in the UTSHC classification reverted to Stage 1 as a result of the treatment.

TABLE 6

| Initial Wound Area | |
|---|---|
| Mean | 6.08 ± 6.54 cm$^2$ |
| Median | 3.92 cm$^2$ |
| Range | 1.08-25.95 cm$^2$ |
| Final Wound Area at 21 days of treatment | |
| Mean | 3.01 ± 5.08 cm$^2$ |
| Median | 0.98 cm$^2$ |
| Range | 0.0-18.90 cm$^2$ |
| Response | |
| 100% closure | 4/15 (27%) |
| 75% closure | 6/15 (40%) |
| Percent Wound Reduction | |
| Mean | 67.7 ± 26.4 |
| Median | 69.8 |
| Range | 19-100 |
| 100% granulation | 14/15 |
| % granulation (mean) | 99.0 ± 3.87 |

After cessation of treatment at 3 weeks, patients were followed for an additional period that ranged up to 12 weeks. Using closure as an endpoint, 9 out of 15 (60%) responded to the hydrogel. Of the 6 who were considered treatment failures based on the intention to treat protocol, one patient was non-compliant with treatment, two were lost to follow-up during the third week of the study, and the other 3 were lost to follow-up during the next 9 weeks. These results show that the hydrogel containing the botanicals as described in example 1 facilitates wound healing.

Example 4B: Additional Use of Hydrogel in Human Subjects

A study was performed to evaluate the efficacy and safety of a hydrogel containing botanicals as described in example 1 (composition 1), as compared to ActivHeal (a marketed hydrogel product comprising similar ingredients that does not contain the ABI, (hereinafter composition 2), for the treatment of diabetic foot ulcers.

The study was a randomized, controlled, multicenter study conducted in accordance with Good Clinical Practice Guidelines at 7 investigative sites in Israel. A total of 82 patients ≥18 years of age with DFU were enrolled and randomized 1:1 to twice-weekly treatment with either composition 1 or 2 for a 4 week period. The investigators, study staff, and patients, were blinded to the treatment assignment. In addition to gel application, all patients underwent standard wound therapy (SWT) twice a week that included any necessary debridement of the DFU. Patients were fitted with and instructed to use an offloading shoe throughout study participation to avoid weight-bearing on the study ulcer.

Prior to randomization, patients underwent SWT during a 2-week screening period. Those whose DFU wound area had not healed by >30% during the 2-week screening could participate as long as they met other eligibility criteria. The major eligibility criteria included: Type 1 or 2 diabetes mellitus, presence of non-infected Wagner Grade I or II DFU for at least 60 days, HbA1c<10%, no altered immunity, no osseous or vascular procedures within 30 days before screening, no systemic antibiotics for an infection in the same foot as the study ulcer within 14 days prior to the screening visit.

During the 4-week randomized treatment period, approximately 2-3 mm thickness of gel (composition 1 or 2) across the entire wound bed gel was applied twice weekly and covered in gauze, to keep the wound moist until the next wound dressing. The maximum amount of gel to be used for any one treatment was 25% of the 3.75 gm tube which was dispensed weekly at study visits. Patients were examined weekly by the investigative site staff for wound size, conversion of wound base, and infection during the 4 weeks of study treatment after the baseline visit. Following the blinded 4 week part of the study, investigators were free to choose SWT or other treatments including open-label Composition 1, and then patients were followed at 8 and 12 week visits, or following wound closure, whichever occurred earlier.

The safety of Composition 1 compared to Composition 2 was evaluated in terms of adverse events (AEs), serious AEs, treatment compliance, tolerability (e.g. dropouts due to AEs), changes from baseline in vital signs, physical examination and lab assessments. Efficacy was evaluated after 4 weeks of SWT plus twice-weekly gel application in terms of percent wound closure and percent conversion of the wound bed to granulation tissue.

Upon completion of the 4 week blinded treatment period, all patients whose DFU wounds had not fully closed (with the exception of one patient) were treated with Composition 1 (open-label). Patients were followed at 8 and 12 week visits, or following wound closure, whichever occurred earlier.

Safety Analysis: All patients who received at least one dose of Compositions 1 or 2 were included. AEs were coded according to the MedDRA (v18.1) dictionary, organized by system organ class, preferred term and study group. Abnormal laboratory values were recorded as "AEs" on the case report form if they were judged to be clinically significant and/or if medical intervention was necessary. The Chi-square test was used to test the statistical significance of the difference between groups in the incidence of AEs.

Assessments for infection of the study DFU occurred at each visit and were performed after the cleaning and/or debridement of the wound. The diagnosis of wound infection was left to the discretion of the site Investigator according to classic symptoms and signs (e.g. purulent drainage, erythema, warmth, exudation, odor, pain, fever, and leukocytosis).

Wound Evaluation: Wounds were assessed for area and depth at each study visit (using the Opsite Flexigrid System for area and disposable gauges for depth). Study Staff were specifically trained on the method for measuring wound size and had periodic reviews of the procedure to minimize variability between evaluators. The progress of wound healing was calculated from the date of the baseline visit (first study treatment) to the end of the 4-week treatment period and continued to be assessed until the last follow-up visit or until total wound closure. For confirmation of wound assessments, a photograph was taken with a camera provided by the sponsor. For each photograph of an ulcer, an adhesive disposable ruler was placed alongside the wound bed to provide a calibration.

The Opsite Flexigrid System was also used to measure the percent conversion of the DFU to granulation tissue at each visit. Conversion of the ulcer wound bed tissue to granulation tissue was assessed by the Investigator according to the accepted clinical definition of granulation tissue, defined as healthy red tissue in the wound bed not covered by fibrotic or necrotic film.

Efficacy was analyzed in the intention-to-treat (ITT) population, which included all patients who received at least one dose of study gel and had at least one of the required weekly assessments after study gel treatment was initiated.

Study Results

A total of 82 patients were randomized (40 to the Composition 1 group; 42 to the Composition 2 group) and received at least one dose of study gel (Safety Population). Overall, 56 AEs were reported by 35 patients. In patients treated with Composition 1, 18 (45.0%) experienced 29 AEs compared to 17 (40.5%) with 27 AEs in the Composition 2 group (p=0.6789).

Wound healing was evident in both groups by the first treatment week. At the end of the 4 week treatment period, patients (modified intent-to-treat (mITT) population) treated with Composition 1 had a 52.0% (±37.6%) reduction in wound area compared to baseline (p<0.0001, paired T-test). Those in the Composition 2 group had a 36.0% (±52.0%) reduction in wound area (p=0.0006). The between group difference at Week 3 was statistically significant (p=0.0415, ANCOVA adjusted for age, gender, baseline wound area, and wound age) and at 4 weeks it trended toward significance.

Likewise, for the per protocol (PP) population, patients in the Composition 1 group had a 53.4% (±37.9%) reduction from baseline in wound area at Week 4 (p<0.0001 compared to baseline) compared with a 36.0% (±52.0%) reduction for patients in the Composition 2 group (p=0.0006 compared to baseline). The difference between groups in the PP population at Week 3 was statistically significant (p=0.035, ANCOVA adjusted for age, gender, baseline wound area, and wound age), and approached significance at Week 4 (p=0.067, ANCOVA adjusted for age, gender, baseline wound area, and wound age).

FIG. 2 shows that the accelerated wound healing in the Composition 1 group was sustained throughout the 4 week treatment period, in that the wound size steadily decreased after Week 1. By contrast, the magnitude of improvement in the hydrogel alone group (Composition 2) began to plateau after treatment Week 2. P values shown are for the difference between the treatment groups at 3 and 4 weeks and are adjusted for age, gender, baseline wound area, and wound age.

The percent conversion of DFU wounds to granulation tissue, as assessed by the Investigator according to the accepted clinical definition of granulation tissue (i.e., healthy red tissue in the wound bed not covered by fibrotic or necrotic film) at Week 4 of treatment was similar in both groups: 97.2% in the Composition 1 and 92.5% in the Composition 2 group.

Patients whose wounds had not completely closed after the double-blinded 4 week treatment period were permitted (if recommended by the Investigator) to continue with open-label Composition 1 plus SWT twice weekly for up to 8 additional weeks, provided they agreed to return at Weeks 8 and 12 for wound assessments. Two patients who did not show up for follow-up visits were excluded from this exploratory analysis. No study visits occurred during the monthly intervals of the follow-up, thus, medication compliance, wound infection, debridement, off-loading, etc., were not recorded during this period. Overall, changes in absolute wound area from baseline to Week 12 were highly significant, regardless of the initial randomization assignment, with both groups achieving >54% reductions in wound area from baseline (p<0.003; PP populations). Complete wound closure occurred in 51% of all patients at Week 12.

By Weeks 8 and 12, patients initially assigned to the composition 1 group (n=23) who continued with treatment had further significant reductions in wound area (p<0.0001) achieving average wound closure of 77%. Importantly, patients initially assigned to hydrogel (n=22) who received composition 1 during the open-label extension phase experienced significant incremental reductions in wound area at Week 8 (p<0.0001) and Week 12 (p=0.0008), achieving average wound closure of 90% (per protocol population, analysis removed subjects assessed to be non-compliant with treatment).

The results from this randomized, controlled, multicenter clinical study in 82 patients with DFU demonstrate that Composition 1 compared favorably with the marketed Composition 2 formulated without botanicals. Designed to maintain wound moisture, prevent microbial contamination, and facilitate wound healing in patients with DFU, both Compositions 1 and Composition 2 (without botanicals) were well-tolerated and demonstrated an excellent and similar safety profile. The AEs in both groups were generally mild and judged to be unrelated to study medication. No clinically significant abnormalities were observed in safety labs, vital signs or physical examinations and no differences were observed in these parameters when comparing treatment groups. Severe and serious AEs were uncommon and none were attributed to application of either of the study gels.

Overall, the improvement in wound healing in the Composition 1 arm was significantly improved over the Composition 2 arm in what is a clinically relevant effect size. Moreover, patients who were given the opportunity to utilize Composition 1 in an open label fashion for an additional two months after the conclusion of the randomized, controlled 4-week treatment period experienced incremental improvement in wound healing after the controlled period of the study, suggesting a sustained clinical benefit and incremental improvement of Composition 1 application in patients with chronic resistant diabetic foot ulcers.

Some embodiments relate to hydrogel composition comprising extracts of *Sambucus nigra, Centella asiatica* and *Echinacea purpurea*; and at least 50% water, Optionally an embodiment relates to a hydrogel composition comprising extracts of *Sambucus nigra, Centella asiatica* and *Echinacea purpurea*; and at least 50% water, wherein the hydrogel composition has a synergistic effect relative to the hydrogel without the extracts of *Sambucus nigra, Centella asiatica* and *Echinacea purpurea*; and to the extracts of *Sambucus nigra, Centella asiatica* and *Echinacea purpurea* in a non-hydrogel form. Optionally, the composition comprises between 60% and 90% water. Optionally, the extracts of *Sambucus nigra, Centella asiatica* and *Echinacea purpurea* are water-extracted alcoholic extracts. Optionally, the composition has a pH of below 6.0, optionally, a pH of above 5.0. Optionally, the extracts of *Sambucus nigra, Centella asiatica* and *Echinacea purpurea* are present in total in an amount of between 1% and 30% of the composition. Optionally, the extracts of *Sambucus nigra, Centella asiatica* and *Echinacea purpurea* are present in an amount of between 5% and 15% of the composition. Optionally, the extracts of *Sambucus nigra, Centella asiatica* and *Echinacea purpurea* are present in an amount of about 7% of the composition. Optionally, the extracts of *Sambucus nigra, Centella asiatica* and *Echinacea purpurea* are present in a ratio of about 7:2:1 *Sambucus nigra, Centella asiatica* and *Echinacea purpurea*. Optionally, the composition further comprises a gelling agent. Optionally, the gelling agent is selected from the group consisting of propylene glycol, guar gum, alginic acid, sodium alginate, potassium alginate, ammonium alginate, calcium alginate, agar, carrageenan, and gelatin. Optionally, the composition further comprises a carrier. Optionally, the carrier is maltodextrin. Optionally, the compositions has a viscosity of 120,000 centipoise (cps) or below. Optionally, the composition is for treating a wound by administering to a subject in need thereof a therapeutically effective amount of the composition. Optionally, the wound is selected from the group consisting of: diabetic foot ulcers, leg ulcers, pressure ulcers/sores, 1st and 2nd degree partial thickness burns, stomata and joint inflammation. Optionally, the wound is selected from the group consisting of: a wound as a result of acute trauma, a surgical incision, a minor abrasion, a minor laceration, a minor cut, a minor scald and a minor burn. Optionally, the wound is selected from the group consisting of a surgical wound, periodontal disease, an anal fissure and hemorrhoids. Optionally, the wound is an oral wound or osteonecrosis of the jaw. Optionally, the oral wound results from a chronic disease, periodontitis, or following periodontal surgery, dental implantation or dental extraction. Optionally, the leg ulcer is selected from the group consisting of: a venous stasis ulcer, an arterial ulcer and a leg ulcer of mixed etiology. Optionally, the pressure ulcer is an ulcer of partial or full thickness. Optionally, the composition is applied once every 2 to 3 days. Optionally, the composition is applied for a period of at least two weeks. Optionally, the composition is applied in a layer having thickness of about 2 mm. Optionally, the wound is covered with a bandage. Optionally, the composition is removed by washing once every 2 to 4 days. Optionally, the composition is for increasing granulation in a wound.

Some embodiments relate to a method for manufacture of a composition described herein comprising:
 a. obtaining water/alcoholic extracts of *Sambucus nigra, Centella asiatica* and *Echinacea purpurea*;

b. forming a blend of the three water/alcoholic extracts of *Sambucus nigra*, *Centella asiatica* and *Echinacea purpurea*;

c. forming an aqueous extract from the blend of the three water/alcoholic extracts; and d. admixing the aqueous extract with water and at least one gelling agent to form a hydrogel Some embodiments relate to a packaged, sterile bandage comprising: a fabric bandage, a composition described herein, and a sterile packaging surrounding said fabric bandage which prevents the penetration of microbes.

Some embodiments relate to a method for treating a wound comprising topically administering to a subject in need thereof a therapeutically effective amount of a composition described herein. Optionally, the wound is selected from the group consisting of: diabetic foot ulcers, leg ulcers, pressure ulcers/sores, 1st and 2nd degree partial thickness burns, stomata and joint inflammation. Optionally, the wound is selected from the group consisting of: a wound as a result of acute trauma, a surgical incision, a minor abrasion, a minor laceration, a minor cut, a minor scald and a minor burn. Optionally, the wound is selected from the group consisting of a surgical wound, periodontal disease, an anal fissure and hemorrhoids. Optionally, the wound is an oral wound or osteonecrosis of the jaw. Optionally, the oral wound results from a chronic disease, periodontitis, or following periodontal surgery, dental implantation or dental extraction. Optionally, the leg ulcer is selected from the group consisting of: a venous stasis ulcer, an arterial ulcer and a leg ulcer of mixed etiology. Optionally, the pressure ulcer is an ulcer of partial or full thickness. Optionally, the composition is applied once every 2 to 4 days. Optionally, the composition is applied for a period of at least two weeks. Optionally, the composition is applied in a layer having thickness of about 2 mm. Optionally, the method further comprises covering the wound with a bandage. Optionally, the method further comprises removal of the composition by washing once every 2 to 3 days.

Some embodiments relate to a method for increasing granulation in a wound comprising administering to a patient in need thereof a composition described herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A hydrogel composition comprising extracts of *Sambucus nigra*, *Centella asiatica* and *Echinacea purpurea*; and at least 50% water.

2. A hydrogel composition comprising extracts of *Sambucus nigra*, *Centella asiatica* and *Echinacea purpurea*; and at least 50% water, wherein the hydrogel composition has a synergistic effect relative to the hydrogel without the extracts of *Sambucus nigra*, *Centella asiatica* and *Echinacea purpurea*; and to the extracts of *Sambucus nigra*, *Centella asiatica* and *Echinacea purpurea* in a non-hydrogel form.

3. The composition according to claim 2 comprising between 60% and 90% water.

4. The composition according to claim 2 wherein the extracts of *Sambucus nigra*, *Centella asiatica* and *Echinacea purpurea* are water-extracted alcoholic extracts.

5. The composition according to claim 2 having a pH of below 6.0.

6. The composition according to claim 5 having a pH of above 5.0.

7. The composition according to claim 2 wherein the extracts of *Sambucus nigra*, *Centella asiatica* and *Echinacea purpurea* are present in total in an amount of between 1% and 30% of the composition.

8. The composition according to claim 7 wherein the extracts of *Sambucus nigra*, *Centella asiatica* and *Echinacea purpurea* are present in an amount of between 5% and 15% of the composition.

9. The composition according to claim 8 wherein the extracts of *Sambucus nigra*, *Centella asiatica* and *Echinacea purpurea* are present in an amount of about 7% of the composition.

10. The composition according to claim 2 wherein the extracts of *Sambucus nigra*, *Centella asiatica* and *Echinacea purpurea* are present in a ratio of about 7:2:1 *Sambucus nigra*, *Centella asiatica* and *Echinacea purpurea*.

11. The composition according to claim 2 further comprising a gelling agent.

12. The composition according to claim 11 wherein the gelling agent is selected from the group consisting of propylene glycol, guar gum, alginic acid, sodium alginate, potassium alginate, ammonium alginate, calcium alginate, agar, carrageenan, and gelatin.

13. The composition according to claim 2 further comprising a carrier.

14. The composition according to claim 13 wherein the carrier is maltodextrin.

15. The composition according to claim 2 having a viscosity of 120,000 centipoise (cps) or below.

16. A method for manufacture of a composition according to claim 1 comprising:

a. obtaining water/alcoholic extracts of *Sambucus nigra*, *Centella asiatica* and *Echinacea purpurea*;

b. forming a blend of the three water/alcoholic extracts of *Sambucus nigra*, *Centella asiatica* and *Echinacea purpurea*;

c. forming an aqueous extract from the blend of the three water/alcoholic extracts; and d. admixing the aqueous extract with water and at least one gelling agent to form a hydrogel.

17. A packaged, sterile bandage comprising: a fabric bandage, a composition according to claim 2 and a sterile packaging surrounding said fabric bandage which prevents the penetration of microbes.

18. A method for treating a wound comprising topically administering to a subject in need thereof a therapeutically effective amount of a composition according to claim 2.

19. The method according to claim 18 wherein the composition is applied once every 2 to 4 days.

20. A method for increasing granulation in a wound comprising administering to a patient in need thereof a composition according to claim 2.

* * * * *